US006284896B1

(12) United States Patent
Mantegani et al.

(10) Patent No.: US 6,284,896 B1
(45) Date of Patent: *Sep. 4, 2001

(54) ABEO-ERGOLINE DERIVATIVES AS 5HT1A LIGANDS

(75) Inventors: Sergio Mantegani, Milan; Tiziano Bandiera, Gamboló ; Enzo Brambilla, Mariano Comense; Carla Caccia, Gallarate; Nicola Carfagna, Nerviano, all of (IT)

(73) Assignee: Pharmacia & Upjohn S.p.A., Milan (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/998,867

(22) Filed: Dec. 29, 1997

Related U.S. Application Data

(63) Continuation of application No. 08/553,545, filed as application No. PCT/EP95/01398 on Apr. 13, 1995, now abandoned.

(30) Foreign Application Priority Data

Apr. 18, 1994 (GB) .................................................. 9407637

(51) Int. Cl.$^7$ ................................................. C07D 487/06
(52) U.S. Cl. ............................................................ 548/421
(58) Field of Search .............................. 548/421; 514/410

(56) References Cited

U.S. PATENT DOCUMENTS

| 4,317,912 | 3/1982 | Temperilli et al. . |
| 4,785,001 | 11/1988 | Temperilli et al. . |
| 4,839,363 | 6/1989 | Brambilla et al. . |
| 4,847,253 | 7/1989 | Buonamici et al. . |
| 4,859,678 | 8/1989 | Mantegani et al. . |
| 5,210,194 | 5/1993 | Mantegani et al. . |
| 5,430,031 | 7/1995 | Mantegani et al. . |

FOREIGN PATENT DOCUMENTS 1 482 871   8/1977   (GB) .

OTHER PUBLICATIONS

Bernardi et al., "5(10 9) ABEO–Ergolines form 9–Hydroxy–ergolines", J.C.S. Chem. Comm., 1976, p. 570.

*Primary Examiner*—Patricia L. Morris
(74) *Attorney, Agent, or Firm*—Oblon, Spivak, McClelland, Maier & Neustadt, P.C.

(57) ABSTRACT

There are provided compounds of formula (I), wherein $R_1$ is a hydrogen, chlorine or bromine atom or a methyl, methylthio, hydroxy, cyano or carboxamido group; $R_2$ is $C_1$–$C_3$ alkyl or an alkyl group; $R_3$ and $R_4$ are independently a hydrogen atom, a $C_1$–$C_5$ alkyl group, a $C_3$–$C_5$ alkenyl group, a $C_5$–$C_6$ cycloalkyl $C_1$–$C_3$ alkyl group, a phenyl-$C_3$–$C_5$ alkenyl or phenyl group: which groups are optionally substituted by $C_1$–$C_3$ alkyl, $C_1$–$C_3$ alkoxy, triflouromethyl, hydroxy or amino group; or a group of formula (a), wherein $R_6$ is hydrogen atom or a $C_1$–$C_3$ alkyl group and $R_7$ is a phenyl group, a substituted phenyl group as described above or a heterocyclic ring, $R_5$ is a hydrogen or bromine atom or an organic residue and R is H or an organic residue, or a pharmaceutically acceptable salt thereof. A process for their preparation and the pharmaceutical compositions comprising them are also provided.

9 Claims, No Drawings

ABEO-ERGOLINE DERIVATIVES AS 5HT1A LIGANDS

This application is a Continuation of application Ser. No. 08/553,545, filed on Dec. 14, 1995, now abandoned, which was filed as International Application No. PCT/EP95/01398, filed on Apr. 13, 1995.

This invention relates to new 5(10→9)abeo-ergoline derivatives, to processes for their preparation, to their use as medicaments and to a pharmaceutical composition containing them. The novel compounds act upon the central nervous system by binding to 5-$HT_{1A}$ receptors and hence can be used for the management of central nervous system pathologies.

The novel compounds of this invention have the formula I

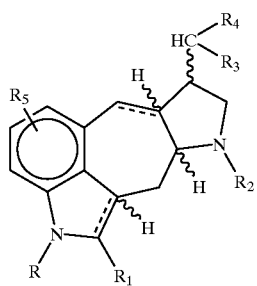

I wherein
$R_1$ is a hydrogen, chlorine or bromine atom or a methyl, methylthio, hydroxy, cyano, carboxamido or nitro group;
$R_2$ is $C_1$–$C_3$ alkyl or an allyl group;
$R_3$ and $R_4$ are independently a hydrogen atom, a linear or branched $C_1$–$C_5$ alkyl group, a linear or branched $C_3$–$C_5$ alkenyl group, a $C_5$–$C_6$ cycloalkyl $C_1$–$C_3$ alkyl group, a phenyl-$C_1$–$C_3$ alkyl, a phenyl-$C_3$–$C_5$ alkenyl or phenyl group: which groups are optionally substituted by a $C_1$–$C_3$ alkyl, $C_1$–$C_3$ alkoxy, trifluoromethyl, hydroxy or amino group: or a group of the formula

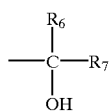

wherein
$R_6$ is a hydrogen atom or a $C_1$–$C_3$ alkyl group and $R_7$ is a phenyl group, a substituted phenyl group as described above or a heterocyclic ring having 5- or 6-ring members including 1 or 2 heteroatoms independently selected from oxygen, sulphur and nitrogen; $R_5$, which can be in the 12, 13 or 14 position, is a hydrogen, bromine, fluorine or iodine atom or a methoxy, cyano, carboxamido, nitro, methylthio or trifluoromethyl group or a aroup of the formula $NR_8R_9$, wherein $R_8$ and $R_9$ are independently a hydrogen atom or a $C_{1-3}$ alkyl, acetyl, trifluoracetyl or methanesulphonyl group. R is a hydrogen atom, a $C_{1-5}$ linear or branched alkyl group, a methanesulphonyl group, an acetyl group or a group of formula —C(O)—$NR_8R_9$ wherein $R_8$ and $R_9$ are as defined above. The dotted line represents the optional presence of a double bond at position 9–10 and/or 2–3.

In the case where a single bond is present in the 9–10 position, the compounds of the invention are of the formula I'

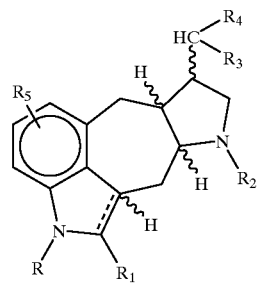

I' wherein
R, $R_1$, $R_2$, $R_3$, $R_4$ and $R_5$ have the above meanings. The wavy lines (∿∿) mean that the hydrogen atoms and the $CHR_3R_4$ group may be at the α or β position with respect to the plane of the rings.

In the case where a single bond is present in position 2,3, the compounds of the invention are of the formula I"

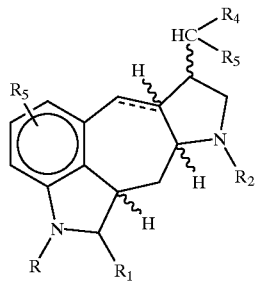

I"

wherein
$R_1$ is hydrogen or a methyl group and $R_2$, $R_3$, $R_4$, $R_5$ and R have the aforementioned meanings.

Pharmaceutically acceptable salts of these abeo-ergoline derivatives are included in the invention.

In the definitions of $R_2$, $R_3$, $R_4$ and R, $C_1$–$C_3$ and $C_1$–$C_5$ alkyl groups are intended to include methyl, ethyl, n-propyl, i-propyl, butyl, i-butyl, cyclopropyl and methylcyclopropyl groups.

In the definitions of $R_3$ and $R_4$, phenyl-$C_1$–$C_3$ alkyl group encompasses benzyl and phenethyl groups; phenyl-$C_3$–$C_5$ alkenyl group is intended to include phenylallyl, phenyl butenyl and phenylpropenyl group. The heterocyclic ring which $R_7$ may represent is, for example, a furanyl, imidazolyl, pyranyl, thienyl, pyrrolyl, pyrazolyl, isothiazolyl, isoxazolyl, pyridyl, pyrazinyl, pyrimidinyl, pyridazinyl, morpholinyl or thiopyranyl group. More preferred compounds are those of the formula I' wherein $R_1$ represents a hydrogen atom, or a cyano or carboxamido group, $R_2$ represents a methyl group, $R_3$ represents a hydrogen atom, $R_4$ represents a group of the formula —CH(OH)Ph, $R_5$ represents a hydrogen, fluorine or iodine atom or a methoxy, methylthio, trifluoromethyl, carboxamido, or nitro group, or a group of the formula $NR_8R_9$, wherein $R_8$ and $R_9$ are independently a hydrogen atom or a $C_{1-3}$ alkyl, acetyl, methanesulphonyl or trifluoroacetyl group. The hydrogen at position 5 and the residue at position 8 are both β.

The present invention also provides a process for the production of the compounds of formula I and their acid addition salts, which process comprises a) reacting a compound of formula II

II wherein $R_2$, $R_3$ and $R_4$ have the meanings given above, with a reducing agent such as sodium amalgam in ethanol, aluminium amalgam in aqueous THF (tetrahydrofuran), magnesium in methanol or ethanol at a temperature ranging from 0° to 80° C.

According to the present invention, compounds of formula II are prepared by reaction of an alkaline salt of a compound of formula III

III wherein $R_2$ is as defined above, either with a compound of formula $R_3Y$, wherein $R_3$ has the meaning given above and Y is a leaving group such as an iodine or bromine atom, or a mesyloxy or tosyloxy group;

or with a compound of the formula R—C(O)—$R_7$ wherein $R_6$ and $R_7$ have the meanings given above and, if desired, reacting an alkaline salt of the resultant compound either with a compound of the formula $R_4Y$, wherein $R_4$ and Y are as defined above, or with a compound of the formula NC(O)$R_7$ wherein $R_6$ and $R_7$ have the meanings given above.

The alkaline salts can be obtained by reaction with strong base such as NaH, KH, ButLi or CH$_3$Li in a solvent such as THF, HMPA (hexamethylphosphotriamide) or DME (dimethoxyathane) at a temperature ranging from −800° C. to 0° C.

The reactions for preparing a compound of the formula II are usually carried out in an anhydrous solvent such as THF, HMPA or DME at a temperature of from −80° C. to room temperature, for a period of from 1 hour to 24 hours.

A compound of the formula III may be prepared by reacting a compound of formula IV

IV wherein $R_2$ is as defined above, with oxidizing agents such as hydrogen peroxide in solvents such as methanol, ethanol or acetic acid or with peroxy acids such as m-chloroperbenzoic or peracetic acid in solvents such as DMF, ethanol or chloroform or with sodium periodate in aqueous THF.

Compounds of the formula IV may be prepared either by reacting a compound of the formula V

V wherein $R_2$ is as defined above with (PhS)$_2$ and (nBut)$_3$P in a solvent such as dioxane, acetonitrile at reflux, or by reacting a compound of the formula (VI)

VI wherein $R_2$ and Y have the same meanings as above with PhSNa in a solvent such as DMF, DMSO (dimethylsulphoxide) or HMPA at a temperature ranging from 80° C. to 120° C.

The compounds of the formula III may also be prepared by reacting a compound of the formula VI as defined above with PhSO$_2$Na in a solvent such as HMPA or DMSO at a temperature ranging from 80° C. to 140° C.

The present invention also provides processes for converting a compound of the formula I into another compound of the formula I wherein one or more of R, $R_1$ and $R_5$ have been altered.

For example, a conversion may be carried out by reacting a compound of the formula I wherein $R_1$ and $R_5$ are hydrogens, with a chlorinating agent such as N—Cl succinimide or sulphuryl chloride, or a brominating agent such as N—Br succinimide, in an inert solvent such as acetonitrile or chloroform; or with a thiomethylating agent such as freshly prepared methylsulphenyl chloride in a solvent such as THF or chloroform; or with an oxiding agent such as N-Br succinimide in tert-butanol.

Following the above methods compounds of the formula I wherein $R_1$ represents chlorine, bromine, methylthio, and hydroxy group are provided.

When $R_1$ is a hydroxy group, the compounds of formula I exist almost completely in the tautomeric lactam form.

According to the present invention, a compound of formula I, wherein $R_1$ is hydrogen, $R_2$, $R_3$, P and $R_5$ have the aforementioned meanings and R is hydrogen or a $C_{1-5}$ linear or branched alkyl group may be converted into a compound of formula I'', wherein $R_1$, $R_2$, $R_3$, $R_4$, $R_5$, R have the aforementioned meanings by treatment with zinc dust in concentrated hydrochloric acid or with a reducing agent such as sodium borohydride or sodium cyano borohydride in trifluoroacetic acid.

Exploitation of general techniques such as fractional crystallization, or column chromatography separation allows the separation in pure form of the C-3 diasteroisomers.

According the present invention a compound of formula I, wherein R is an acetyl, methanesulphonyl or dimethylaminocarbonyl group may be obtained by the reaction of a compound of formula I'' wherein R is hydrogen with acetyl chloride, acetic anhydride, methanesulphonyl chloride or dimethylaminocarbonyl chloride in a solvent such as pyridine or ethylacetate, whereas for R to be an aminocarbonyl group, a carbamoylating agent such as potassium cyanate in diluted hydrochloric acid is employed.

According to the present invention a compound of formula I, wherein a double bond is present in the 2,3 position and $R_1$, $R_2$, $R_3$, $R_4$, $R_5$ have the above mentioned meanings and R is hydrogen may be converted in a compound wherein R is a $C_1$–$C_5$ linear or branched alkyl group by reaction with the suitable alkyl iodide in the presence of ground potassium or sodium hydroxide in a solvent such as dimethylsulphoxide.

Moreover, a compound of the formula I, wherein $R_1$ is a bromine atom or a methylthio group and $R_5$ is a hydrogen atom, may be converted into another compound of the formula I wherein $R_1$ is a hydrogen or bromine atom or a methylthio group, and $R_5$ represents a bromine atom or a methoxy, a cyano or a carboxamido group, by bromination in glacial acetic acid followed, if necessary, by the reaction of the resultant compound of the formula $I_A$

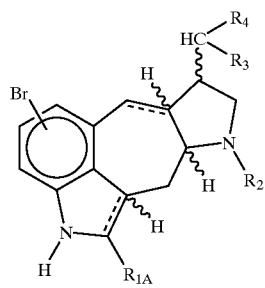

$I_A$ wherein
$R_2$, $R_3$ and $R_4$ are as above defined and $R_{1A}$ is a hydrogen or bromine atom or a methylthio group, with the appropriate nucleophilic agent.

The compounds of the formula $I_A$ wherein $R_{1A}$ represents a hydrogen atom may be obtained from the corresponding compounds of the formula $I_A$ wherein $R_{1A}$ is a bromine atom or a methylthio group by careful reduction.

The reduction may be carried out using cobalt or nickel hydride in methanol or ethanol.

For example, nucleophilic displacement by means of freshly prepared sodium methoxide or thiomethoxide in DMF or N-methyl-2-pyrrolidinone in the presence of a cuprous salt at 120° C. converted a compound of the formula I', as above defined, into a compound of the formula I wherein $R_5$ is a methoxy or methylthio group.

On the other hand, the reaction of a compound of the formula $I_A$ with a cyanating agent, such as $KCN/Cu_2(CN)_2$ in DMF or N-methyl-2-pyrrolidinone, and in the presence of cyano nickel complexes afforded a compound of the formula I wherein $R_5$ is a cyano group.

A compound of the formula I wherein $R_5$ is a carboxamido group can be prepared by reacting a compound of the formula I wherein $R_5$ is a cyano group with hydrogen peroxide in methanol in the presence of potassium carbonate or with KOH in refluxing tert-butanol or by heating in phosphoric acid. A compound of the formula I wherein $R_5$ is not a hydrogen or bromine atom and $R_1$ is a hydrogen atom may also be prepared by reduction of the corresponding compound of the formula I wherein $R_1$ is a methylthio group or a bromine atom.

The invention provides a method to convert a compound of formula $I_B$

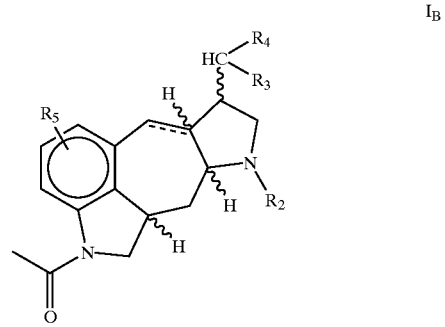

$I_B$ wherein
$R_2$, $R_3$, $R_4$ have the above mentioned meanings and $R_5$ is hydrogen into a compound of formula I wherein a double bond is present in the 2,3 position and $R_1$ is hydrogen and $R_2$, $R_3$, $R_4$ have the meanings as defined above and $R_5$ is a nitro, amino, dimethyl, diethylamino, acetylamino or a methanesulphonyl amino group or a fluorine or iodine atom.

The conversion is performed by the reaction of the compound of formula $I_B$ with a nitrating agent such as acetyl nitrate or nitroniosulphate in a solvent such as acetic acid or sulphuric acid affording in such manner compound $I_B$ wherein $R_5$ is a nitro group.

Careful reaction with Raney nickel in the presence of sodium hydroxide in ethanol as solvent affords a compound of formula I wherein a double bond is present in the 2,3 position, $R_1$ is hydrogen, $R_2$, $R_3$, $R_4$, have the above mentioned meanings and $R_5$ is an amino group and R is a hydrogen atom or, conversely, compounds of this structure can be obtained by reaction with potassium t-butoxide in DMSO followed by reduction of the nitro group by means of a reducing agent such as zinc dust or stannous chloride in hydrochloric acid.

Further reaction with suitable reagents such as acetylchloride or methanesulphonylchloride in a solvent such as pyridine affords a compound wherein $R_5$ is an acetyl or methanesulphonyl group, whereas reaction with formaldehyde or acetaldehyde in the presence of a reducing agent such as sodium cyanoborohydride in a solvent such as methanol or ethanol provides the preparation of compounds wherein $R_5$ is a dimethyl or diethylamino group.

Conversely compounds wherein $R_5$ is a fluorine atom-or an iodine atom may be obtained by reaction with nitrosating agent such as sodium or potassium nitrite in tetrafluoroboric acid or in sulphuric acid in the presence of potassium periodide.

Conversely compounds wherein $R_5$ is a bromine or iodide atom can be converted into compounds wherein $R_5$ is a trifluoromethyl group by reaction with sodium trifluoro acetate in solvents such as hexamethylphosphotriamide or N-methyl pyrrolidin-2-one in the presence of cuprous iodide or bromide at 120–150° C.

The starting compounds of the formulae V and VI are known compounds (see GB1482871) or may be prepared by known reactions from known derivatives.

The compounds of the formula I and their acid addition salts show selective and high affinity for 5-$HT_{1A}$ receptors and display negligible affinity towards $\alpha_1$, $\alpha_2$, $D_1$, $D_2$ receptors.

Therefore, the compounds provided by this invention can be used in the treatment of CNS diseases such as anxiety, sleep and sexual disorders, psychosis, personality disorders, drug addiction, age associated memory impairment, ischemic insults, Alzheimer disease. For pharmaceutical use, the compounds of the formula I may be used as such or in the form of physiologically acceptable acid addition salts. Physiologically acceptable acids which may be used in salt formation include maleic, citric, tartaric, fumaric, methane sulphonic, acetic, benzoic, succinic, gluconic, lactic, malic, mucoic, glutammic, ascorbic as organic acids or hydrochloric, hydrobromic, sulphuric or phosphoric as inorganic acids. Among the addition salts obtained by employing acids hydrochoric, sulphoric, methanesulphonic, citric and succinic salts are the most preferred.

The compounds of this invention, or the pharmaceutically acceptable salts thereof, may be used in the manufacture of a medicament for use in the treatment of CNS diseases. A human or animal may thus be treated by a method which comprises the administration thereto of a pharmaceutically effective amount of a compound of formula (I) or salt thereof. The condition of the human or animal can thereby be improved.

The dosage rate may be a daily administration of from 0.1 to 100 mg, more preferably 1 to 25 mg, of active compound.

As already mentioned hereinbefore, the compounds of formula I according to the present invention show interesting pharmacological properties owing to their activity on CNS serotoninergic receptors subtype 5-$HT_{1A}$.

The biochemical and pharmacological profile of the compounds which are the object of the present inve[]ntion was assessed by evaluating their affinity for 5-$HT_{1A}$ receptors.

Receptor Binding Studies

Receptor binding studies were carried out to determine the affinity on the test compounds of formula I.

Experiment 1: Affinity for Serotonin 1A ($^5KT_{1A}$) Receptor [$^3$H-8-Hydroxy-2-dipropylaminotetralin ($^{3-8}$-OH-DPTA)-Binding Test].

Preparation of crude synaptosome fraction and binding assay were conducted in accordance with the method reported in Journal of Neurochemistry, vol. 44, page 1685, 1985 by Hall et al. Freezed hippocampus dissected out from rats were homogenized in 40 volumes of ice cold 5OSM Tris-HCl buffer (pH. 7.4) and the suspension was centrifuged at 500×g for 10 minutes at 0° C.

The supernatant was centrifuged at 40,000×g for 20 minutes at 0° C. and the resulting pellet was homogenized in 40 volumes of the above buffer and incubated at 37° C. for 10 minutes.

After completion of reaction, the suspension was centrifuged at 40,000×g for 20 minutes at 0° C. The resulting pellet was washed twice by resuspension in 40 volumes of the above buffer and centrifugation, and finally suspended in 60 volumes of ice-cold 50 mM Tris-HCl buffer (pH 7.4) containing 1 EM manganese chloride for use in the next assay.

To the aliquots (900 µl) of synaptosome membranes solution were added 50 µl of tritiated 8-OH-DPAT solution at the terminal concentration of 0.2 nM and 50 µl of test compound solution or 50 µl of its medium, and incubated at 37° C. for 10 minutes. Then to the mixture were added 5 ml of ice-cold 50 mM Tris-HCl buffer (pH 7.4) rapidly vacuum-filtered through Whatman$^R$ GF/B. filters and was washed twice with 5 ml of the same buffer. The radioactivity of the residue remaining on the filters was measured by liquid scintillation counter. Non specific binding was determined under the presence of $10^{-5}$M serotonin (5-HT). 50% inhibition concentration ($IC_{50}$) of the test compound was graphically determined. The results are summarized in the Table.

Experiment 2: Affinity for Serotonin 2(5-$HT_2$) Receptor ($^3$H-Ketanserin Binding Test).

Preparation of crude synaptosome fraction and binding assay were conducted according to the method reported in Molecular Pharmacology, vol. 21, page 301, 1981 by Leysen et al.

Freezed cerebral cortex dissected out from rats were homogenized in 30 volumes of ice-cold 0.32M sucrose solution and the suspension was centrifuged at 1000×g for 10 minutes at 0° C. The supernatant was centrifuged at 40,000×g for 20 minutes at 0° C. and the resulting pellets was homogenized in 30 volumes of ice-cold 50 mM Tris-HCl buffer (pH 7.7) and incubated at 37° C. for 10 minutes. The suspension was centrifuged at 40,000×g for 20 minutes at 0° C. again. The resulting pellet was homogenized in 100 volumes of the above buffer and provided as synaptosome membranes solutiofifor the next assay.

To the aliquots (900µ) of synaptosome membranes solution were added 50 µl solution $^3$H-Ketanserin solution at the terminal concentration of 0.2 mM and 50 µl of test compound or its medium, and incubated at 37° C. for 20 minutes. After completion of the reaction, the mixture was rapidly vacuum-filtered through Whatman$^R$ GF/B filters. The filters were washed three times with 5 ml of the above buffer, and then the radioactivity of the residue remaining on the filters was measured by liquid scintillation counter. Non specific binding was determined under the presence of 10 µM of mianserin. 50% inhibition concentration (ICY) of the test compound was graphically determined. The results are summarized in the Table.

Experiment 3: Affinity for Dopamine 2 ($D_2$) Receptor ($^3$H-Spiperone Binding Test).

Preparation of crude synaptosome fraction and binding assays were conducted in accordance with the method reported in European Journal of Pharmacology, vol. 46, page 377, 1977 by I. Creese et al. Freezed corpus striatum dissected out from rats were homogenized in 100 volumes of ice-cold 50 mM Tris-HCl buffer (pH 7.7) and the suspension was centrifuged at 500×g for 10 minutes at 0° C. The supernatant was centrifuged at 50,000×g for 15 minutes at 0° C. and the resulting pellet was homogenized in 100 volumes of the above buffer and then the suspension was centrifuged at 50,000×g for 15 minutes at 0° C. again. The resulting pellet was homogenized in 150 volumes of 50 mM Tris-HCl buffer (pH 7.1) containing 120 mM potassium chloride, 2 mM calcium chloride, 1 mM magnesium chloride, 0.1% ascorbic acid and 10 $\mu$M pargyline. The suspension was incubated at 37° C. for 10 minutes and then provided as synaptosome membranes solution for the next assays. To the aliquots (900 $\mu$l) of synaptosome membranes solution were added 50 $\mu$l of 3H-Spiperone solution at the terminal concentration of 0.2 nM and 50 $\mu$l of test compound solution or 50 $\mu$l of its medium, and incubated at 37° C. for 20 minutes. After completion of the reaction, the mixture was rapidly vacuum-filtered through WhatmanR GF/B filters. The filters were washed three times with 5 ml of the above buffer, and then the radioactivity of the residue remaining on the filters was measured by liquid scintillation counter. Non specific binding was determined under presence of 100 $\mu$M of (L)-Sulpiride 50% inhibition concentration ($IC_{50}$) of the test compound was graphically determined. The results are summarized in the Table.

TABLE

| | Binding Profile $IC_{50}$ nM | | | |
|---|---|---|---|---|
| Example | $D_1$ | $D_2$ | $5-HT_{1A}$ | $5-HT_2$ |
| 3 | 1850 | 940 | 6 | 110 |
| 4 | 1920 | 620 | 330 | 1000 |
| 5 | 2540 | 850 | 800 | 800 |
| 33 | >10000 | >10000 | 6 | >10000 |
| 34 | >10000 | 5000 | 100 | >10000 |
| 35 | >10000 | 6030 | 530 | >10000 |
| 36 | >10000 | 4480 | 100 | >10000 |
| 39 | 7100 | 130 | 6 | 2080 |
| 40 | 2750 | 4870 | 3 | 1240 |
| 42 | >10000 | 2000 | 18 | 1860 |

In therapeutic use the active compounds may be administered orally, rectally, parenterally or topically, preferably orally.

Thus, the therapeutic composition of the present invention may take the form of any of the known pharmaceutical compositions for oral, rectal, parenteral or topical administration.

Compositions for oral administration are the preferred compositions of the invention and these are the known pharmaceutical forms for such administration, for example tablets, capsules, syrups and aqueous or oily suspensions. The excipients used in the preparation of these compositions are the excipients known in the pharmacist's art.

Tablets may be prepared by mixing the active compound with an inert diluent, such as calcium phosphate, in presence of disintegrating agents, for example magnesium stearate, and tabletting the mixture by known methods.

Such tablets, if desired, may be provided with enteric coatings by known methods, for example by the use of cellulose acetate phthalate. Similarly capsules, for example hard or soft gelatine capsules containing the active compound with or without added excipients, may be prepared by conventional means and, if desired, provided with enteric coatings in a known manner. The tablets and capsules may conveniently each contain 2 to 10 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example, arachid oil.

Compositions of the invention suitable for rectal administration are the known pharmaceutical forms for such administration, for example suppositories with cocoa butter or polyethylene glycol bases.

Compositions of the invention suitable for parenteral administration are the known pharmaceutical forms for such administration, for example sterile suspensions or sterile solutions in a suitable solvent.

In some formulations it may be beneficial to use the compounds of the present invention in the form of particles of very small size, for example, as obtained by fluid energy milling.

The following examples illustrate the invention.

The following reaction scheme illustrates the invention.

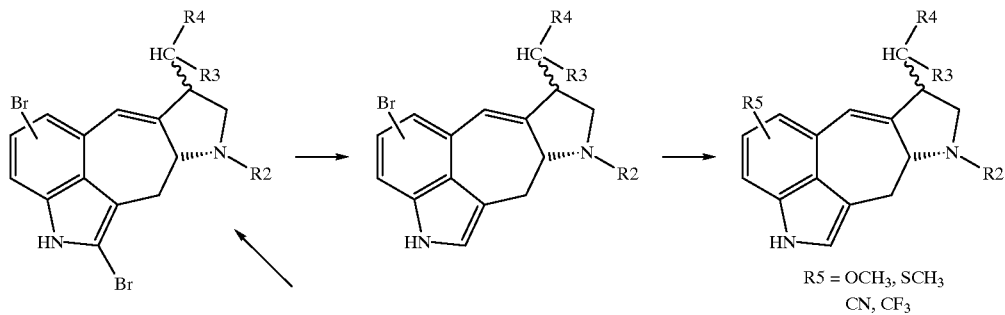

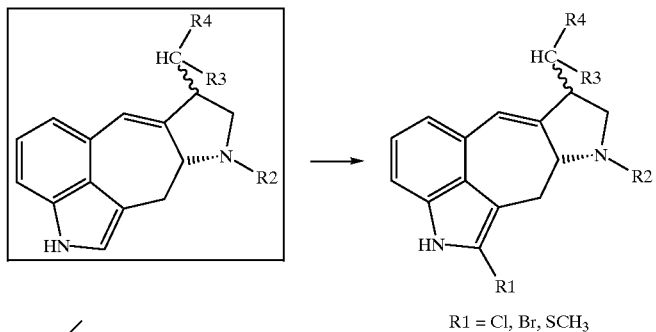

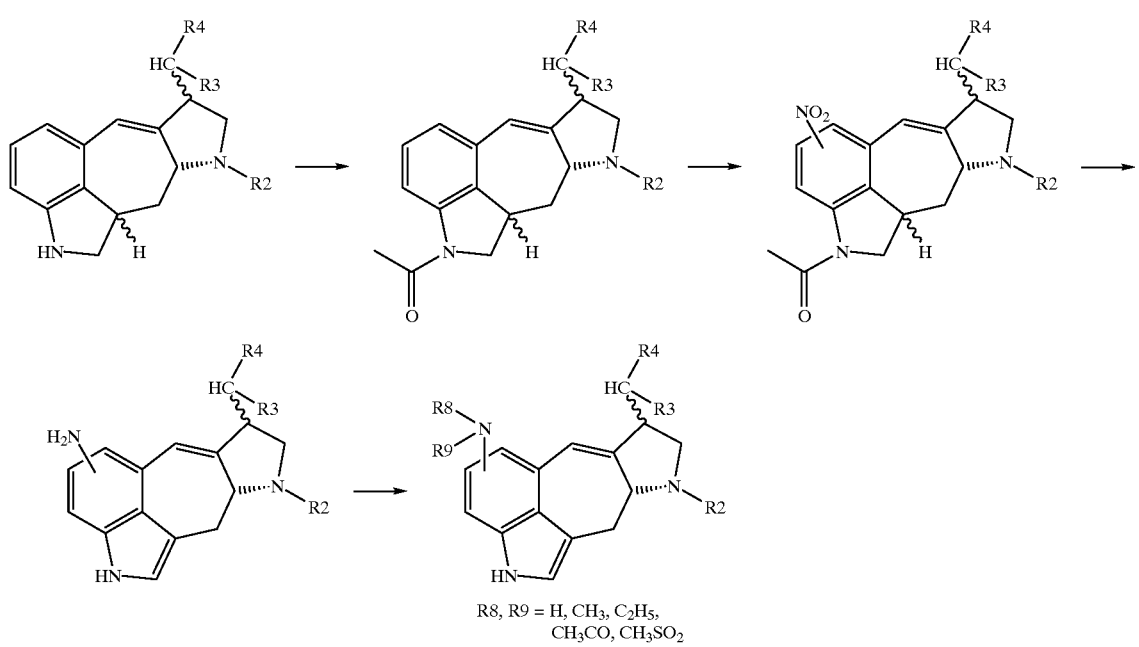

Formulation example of the pharmaceutical composition of tablets:

Tablets containing 10 mg of a compound of formula I can be prepared by the following composition.

| | |
|---|---|
| Compound of example 33 | 10.0 mg |
| Lactose | 60 mg |
| Corn starch | 25 mg |
| Crystalline cellulose | 20 mg |
| Polyvinylpyrrolidone K$_{30}$ | 2 mg |

-continued

| | |
|---|---|
| Talc | 4 mg |
| Magnesium stearate | 0.5 mg |

The active compound is pulverized with an atomizer to make fine powder having an average particle size below 10μ. The fine powder of the active compound, lactose, corn starch and crystalline cellulose are mixed well in a kneader and the kneaded with a binder paste prepared by polyvinylpyrrolidone K$_{30}$. The wet mass is passed through a 200 mesh sieve and then dried in an oven at 50° C. The dry granule containing 3 to 4% of water content is forced through a 24 mesh sieve. Talc and magnesium stearate are mixed and compressed into tablets by using a rotary tabletting machine with a flat punch of 8 mm diameter. Some of the preferred compounds of the present invention are listed below:

5β(10→9)abeo-9,10-Didehydro-6-methyl-8β-methyl-ergoline

5α(10→9)abeo-9,10-Didehydro-6-methyl-8β-methyl-ergoline

5β(10→9)abeo-9,10-Didehydro-6-methyl-8α-methyl-ergoline

5β(10→9)abeo-6-methyl-8β-methyl-10α-ergoline

5β(10→9)abeo-9,10-Didehydro-2-cyano-6-methyl-8β-methyl-ergoline

5β(10→9)abeo-9,10-Didehydro-2-aminocarbonyl-6-methyl-8β-methyl-ergoline

5β(10→9)abeo-9,10-Didehydro-6-methyl-8β-(3-phenyl)propyl-ergoline

5β(10→9)abeo-9,10-Didehydro-2-bromo-6-methyl-8β-methyl-ergoline

5β(10→9)abeo-2,3β-Dihydro-9,10-didehydro-1-aminocarbonyl-6-methyl-8β-methyl-ergoline 5β(10→9)abeo-2,30-Dihydro-9,10-didehydro-1-methanesulphonyl-6-methyl-8β-methyl-ergoline 5β(10→9)abeo-9,10-Didehydro-6-methyl-8β-methyl-12-bromo-ergoline 5β(10→9)abeo-9 10-Didehydro-6-methyl-8α-methyl-12-bromo-ergoline 5β(10→9)abeo-9,10-Didehydro-6-methyl-8β-methyl-13-bromo-ergoline 5β(10→9)abeo-9,10-Didehydro-6-methyl-8β-methyl-12-cyano-ergoline 5β(10→9)abeo-9,10-Didehydro-6-methyl-8β-methyl-12-aminocarbonyl-ergoline 5β(10→9)abeo-9,10-Didehydro-6-methyl-8β-methyl-13-methylthio-ergoline 5β(10→9)abeo-9,10-Didehydro-6-methyl-8β-methyl-12-methoxy-ergoline 5β(10→9)abeo-9,10-Didehydro-6-methyl-8β-methyl-13-methoxy-ergoline 5β(10→9)abeo-6-methyl-8β-methyl-12-methoxy-10β-ergoline 5β(10→9)abeo-9,10-Didehydro-6-methyl-8α-methyl-12-nitro-ergoline 5β(10→9)abeo-9,10-Didehydro-6-methyl-8β-methyl-12-amino-ergoline 5β(10→9)abeo-9,10-Didehydro-6-methyl-8β-methyl-12-methanesulphonylamino-ergoline 5β(10→9)abeo-9,10-Didehydro-6-methyl-8β-methyl-13-methanesulphonylamino-ergoline 5β(10→9)abeo-9,10-Didehydro-6-methyl-8β-methyl-12-fluoro-ergoline 5β(10→9)abeo-9,10-Didehydro-6-methyl-8β-methyl-13-fluoro-ergoline 5β(10→9)abeo-6-methyl-8β-methyl-12-fluoro-10β-ergoline 5β(10→9)abeo-2,3β-Dihydro-9,10-didehydro-6-methyl-8β-methyl-12-fluoro-ergoline 5β(10→9)abeo-2,3-p-Dihydro-9,10-didehydro-6-methyl-8β-methyl-12-trifluoromethyl-ergoline 5β(10→9)abeo-6-methyl-8β-methyl-12-fluoro-10α-ergoline 5β(10→9)abeo-6-methyl-8β-methyl-12-aminocarbonyl-10α-ergoline 5β(10→9)abeo-9,10-Didehydro-6-methyl-8β-methyl-12-iodo-ergoline 5β(10→9)abeo-9,10-Didehydro-6-methyl-8β-methyl-12-trifluoromethyl-ergoline 5β(10→9)abeo-6-methyl-8β-methyl-12-trifluoromethyl-10α-ergoline 5β(10→9)abeo-6-methyl-8β-methyl-12-trifluoromethyl-10β-ergoline

EXAMPLE 1

5β(10→9)abeo-9,10-Didehydro-6-methyl-8β-phenyl thiomethyl-ergoline.

A solution of 22.6 g of 5(10→9)abeo-9,10-didehydro-6-methyl-8β-hydroxymethyl-ergoline and 21 g of diphenyldisulphide and 20 g of tri-n-butylphosphine in 200 ml of acetonitrile was refluxed for 2 hours. The solvent was evaporated off and the oily residue was chromatographed on silica gel eluting with cyclohexane/ethyl acetate 1/1 affording after crystallization from diethyl ether 29 g of the title compound m.p. 147–151° C.

EXAMPLE 2

5β(10→9)abeo-9,16-Didehydro-6-methyl-8β-(phenylsulphonyl)methyl-ergoline.

To a solution of 3.6 g of 5β(10→9)abeo-9,10-didehydro-6-methyl-8β-phenylthiomethyl-ergoline in 50 ml of methanol and 5 ml of methanesulphonic acid was added portionwise 3.5 g of m-chloroperbenzoic acid (50%), at room temperature. After stirring for 2 hours, the solvent was removed and the residue was taken up in ethyl acetate and washed with a saturated solution of sodium hydrogenocarbonate. After washing with brine and drying, the solvent was removed and the crude reaction mixture was filtered on a small pad of silica gel eluting with cyclohexane/ethyl acetate 2/1. Crystallization from diethyl ether yielded 2.1 g of the title compound, m.p. 163–165° C.

EXAMPLE 3

5β(10→9)abeo-9,10-Didehydro-6-methyl-8β-methyl-ergoline.

A mixture of 11.8 g of 5β(10→9)abeo-9,10-didehydro-6-methyl-8β-(phenylsulphonyl)methyl-ergoline and 2.2 g of metallic magnesium and few crystals of mercuric chloride in 200 ml of dry ethanol was stirred for 2 hours at room temperature. After evaporation of the solvent, the residue was partitioned between ethyl acetate and diluted ammonium hydroxide. After washing with brine and drying, concentration yielded 5.8 g of the title compound as shiny crystals, m.p. 214–220° C.

EXAMPLE 4

5β(10→9)abeo-9,10-Didehydro-2-bromo-6-methyl-8β-methyl-ergoline.

To a solution of 2.1 g of 5β(10→9)abeo-9,10-didehydro-6-methyl-8β-methyl-ergoline in 75 ml of dioxane were added portionwise 1.9 g of N-bromo-succinimide. After stirring at 40° C. for 2 hours, the solvent was removed and the residue was chromatographed on silica gel eluting with cyclohexane/acetone 2/1. After crystallization from ethyl acetate 1.3 g of the title compound were obtained, m.p. 78–80° C.

EXAMPLE 5

5β(10→9)abeo-9,10-Didehydro-2-methylthio-6-methyl-8β-methyl-ergoline.

A solution freshly prepared of 5 g of methylsulphenylchloride in 100 ml of methylene chloride was slowly added dropwise to a stirred solution of 11.9 g of 5(10→9)abeo-9,10-didehydro-6-methyl-8β-methyl-ergoline in 300 ml of methylene chloride at −20° C.

After stirring for 1 hour at −20° C., the yellow solution was set aside at room temperature for 1 hour.

After partitioning; with a diluted ammonium hydroxide solution, the organic phase was dried and evaporated.

The residue was crystallized from a mixture of cyclohexane/acetone 211, providing 11.7 g of the title compound, m.p. 77–79° C.

EXAMPLE 6
5β(10→9)abeo-9,10-Didehydro-6-methyl-8β-(2-phenyl) ethyl-ergoline.

To a solution of 3 g of 5β(10→9)abeo-6-methyl-8β-(phenylsulphonyl)methyl-ergoline in 75 ml of tetrahydrofuran at −78° C. were added 9.17 ml of n-butyl lithium 2.5M in hexane.

After one hour at −78° C., a solution of 1.8 g of benzyl bromide in 10 ml of tetrahydrofuran was slowly added and the stirring was continued at −78° C. for 1 hour then set aside for 2 hours at room temperature.

The reaction mixture was diluted with saturated aqueous sodium hydrogenocarbonate solution and extracted with ethyl acetate.

The organic phase was dried over sodium sulphate, concentrated by rotary evaporation and subjected to silica gel chromatography eluting with cyclohexane/ethyl acetate 3/1 furnishing 2.7 g of a mixture of sulphone diastereomers, that was treated with 0.38 g of metallic magnesium and few crystals of mercuric chloride in 50 ml of dry ethanol for 3 hours at room temperature. The solvent was evaporated off and the crude reaction mixture was taken up in ethyl acetate, washed with brine and dried.

After chromatography on a small pad of silica gel eluting with cyclohexane/ethyl acetate 4/1 and further crystallization from diisopropylether, 1.8 g of the title compound were obtained in 76% yield, m.p. 112–115° C.

EXAMPLE 7
5β(10→9)abeo-9,10-Didehydro-6-methyl-8β-(4-buten)-1-yl-ergoline.

Operating as in Example 6, but employing allyl bromide instead of benzyl bromide, the title compound was obtained in 45% yield, m.p. 87–90° C.

EXAMPLE 8
5β(10→9)abeo-9,10-Didehydro-6-methyl-8β-(3-phenyl) propyl-ergoline.

Operating as in Example 6, but employing phenethyl bromide instead of benzyl bromide, the title compound was obtained in 55% yield, m.p. 107–109° C.

EXAMPLE 9
5β(10→9)abeo-9,10-Didehydro-6-methyl-8β-hexyl-1-yl-ergoline.

Operating as in Example 6, but employing n-pentyl bromide instead of benzyl bromide, the title compound was obtained in 35% yield, m.p.

EXAMPLE 10
5β(10→9)abeo-9,10-Didehydro-6-methyl-8β-2(3,4-dimethoxy-phenyl)ethyl-ergoline.

Operating as in Example 6, but employing 3,4-dimethoxy-benzyl bromide, the title compound was obtained in 40% yield, m.p. 121–122° C.

EXAMPLE 11
5β(10→9)abeo-9,10-Didehydro-6-methyl-8β-(2-cyclohexyl) ethyl-ergoline.

Operating as in Example 6, but employing cyclohexylmethyl bromide instead of benzyl bromide, the title compound was obtained in 20% yield, m.p. 88–90° C.

EXAMPLE 12
5β(10→9)abeo-9,10-Didehydro-2-bromo-6-methyl-8β-(2-phenyl ethyl-ergoline.

Operating as in Example 4, but employing 5β(10→9) abeo-9,10-didehydro-6-methyl-8β-(2-phenyl)ethyl-ergoline instead of 5β(10→9)abeo-9,10-didehydro-6-methyl-8β-methyl-ergoline; the title compound was obtained in 65% yield, m.p. 106–108° C.

EXAMPLE 13
5β(10→9)abeo-9,10-Didehydro-6-methyl-8β-(2-methyl) propyl-ergoline.

Operating as in Example 6, but employing isopropyl iodide instead of benzyl bromide, the title compound was obtained in 22% yield, m.p. 118–120° C.

EXAMPLE 14
5β(10→9)abeo-9,10-Didehydro-2-cyano-6-methyl-8β-methyl-ergoline.

To a stirred solution of 4 g of 5β(10→9)abeo-9,10-didehydro-6-methyl-8β-methyl-ergoline in 200 ml of acetonitrile was slowly added a solution of 2.6 g of chlorosulphonyl isocyanate in 20 ml of acetonitrile at room temperature.

After stirring for 80 hours, 8 ml of triethylamine were added at 0° C.

The solution was set aside at 0° C. for 3 hours, then treated with a saturated solution of sodium carbonate and extracted with ethyl acetate. The organic phase was washed with brine, dried and concentrated at small volume providing 2.8 g of the title compound, m.p. 253–255° C.

EXAMPLE 15
5β(10→9)abeo-9,10-Didehydro-2-aminocarbonyl-6-methyl-8β-methyl-ergoline.

To a solution of 1 g of 5β(10→9)abeo-9,10-didehydro-2-cyano-6-methyl-8β-ergoline and 1.5 g of potassium carbonate in 50 ml of ethanol and 10 ml of water was adaed 1.5 ml of hydrogen peroxide (120 vol) at room temperature.

After 3 hours, the solution was concentrated and partitioned between ethyl acetate and brine.

After drying and evaporation of the solvent, the residue was crystallized from acetone yielding 0.6 g of the title compound, m.p, 270–273° C.

EXAMPLE 16
5β(10→9)abeo-9,10-Didehydro-6-methyl-8β-2(2-furyl) ethyl-ergoline.

Operating as in Example 6, but employing 2-furylmethyl chloride instead of benzyl bromide, the title compound was obtained in 30% yield, m.p. 100–103° C.

EXAMPLE 17
5β(10→9)abeo-9 10-Didehydro-6-n-proryl-8β-methyl-ergoline.

Operating as in Example 3, but employing 5β(10→9) abeo-9,10-didehydro-6-n-propyl-8β-(phenylsulphonyl) methyl-ergoline, instead of 5β(10→9)abeo-9,10-didehydro-6-methyl-8β-(phenylsulphonyl)methyl-ergoline, the title compound was obtained in 35% yield, m.p. 176–178° C.

EXAMPLE 18
5β(10→9)abeo-9,10-Didehydro-6-methyl-8β-(2-hydroxy-2-phenyl)ethyl-ergoline.

Operating as in Example 6, but employing benzaldehyde instead of benzyl bromide, the title compound was obtained in 15% yield as a mixture by diastereomers.

EXAMPLE 19
5β(10→9)abeo-9,10-Didehydro-6-methyl-8β-(2-methyl-2-hydroxy)propyl-ergoline.

Operating as in Example 6, but employing acetone instead of benzyl bromide, the title compound was obtained in 20% yield, m.p. 92–94° C.

EXAMPLE 20

5β(10→9)abeo-9 10-Didehydro-2,13-dibromo-6-methyl-8β-methyl ergoline.

To a solution of 10 g of 5β(10→9)abeo-9,10-didehydro-6-methyl-8β-methyl-ergoline in 100 ml of glacial acetic acid were slowly added, at room temperature, 15 g of bromine dissolved in 50 ml of glacial acetic acid.

After 2 hours of stirring at room temperature, the resulting reaction mixture was concentrated and diluted with chloroform and subsequently partitioned with an ammonium hydroxide solution.

The organic phase was dried then the solvent was removed off. The residue was crystallized from ethanol providing 14.3 g of the title compound, m.p. 132–135° C.

EXAMPLE 21

5β(10→9)abeo-9,10-Didehydro-6-methyl-8β-methyl-13-bromo-ergoline.

To a solution of 5 g of 5β(10→9)abeo-9,10-didehydro-2,13-dibromo-6-methyl-8β-methyl-ergoline and 12 g of cobalt dichloride hexahydrate in 100 ml of methanol, 7 g of sodium borohydride were slowly added portionwise at 0° C. The black mixture was stirred for 15 minutes. The precipitate was then filtered through celite and washed with methanol. The reaction mixture was concentrated and partitioned between chloroform and concentrated ammonium hydroxide solution. After drying, the solvent was taken off and the residue was chromatographed on silica gel eluting with cyclohexane/ethyl acetate 3/1.

The fractions containing the product were pooled and the solvent removed.

After crystallization from isopropanol, 2.7 g of the title compound were obtained, m.p. 121–124° C.

EXAMPLE 22

5β(10→9)abeo-9,10-Didehydro-2-thiomethyl-6-methyl-8β-methyl-12-bromo-ergoline and 5β(10→9)abeo-9,10-didehydro-2-thiomethyl-6-methyl-8β-methyl-3-bromo-ergoline;

Operating as in Example 20, but employing 5β(10→9)abeo-9,10-didehydro-2-thiomethyl-6-methyl-8β-methyl-ergoline-instead of 5,(10→9)abeo-9,10-didehydro-6-methyl-8β-methyl-ergoline after a careful column chromatography separation 5β(10→9)abeo-9,10-didehydro-2-thiomethyl-6-methyl-8β-methyl-13-bromo-ergoline was isolated in 45% yield, m.p. 106–108° C. besides 5β(10→9)abeo-9,10-didehydro-2-thiomethyl-6-methyl-8β-methyl-12-bromo-ergoline isolated in 12% yield, m.p. 121–123° C.

EXAMPLE 23

5β(10→9)abeo-9,10-Didehydro-6-methyl-8β-methyl-12-bromo-ergoline.

Operating as in Example 21, but employing 5β(10→9)abeo-9,10-didehydro-2-methylthio-6-methyl-8β-methyl-12-bromo-ergoline instead of 5β(10→9)abeo-9,10-didehydro-2,13-dibromo-6-methyl-8β-methyl-ergoline and nickel chloride hexahydrate instead of cobalt chloride hexahydrate, the title compound was obtained in 25% yield, m.p.136–137° C.

EXAMPLE 24

5β(10→9)abeo-9,10-pidehydro-6-methyl-8β-methyl-12-methoxy-ergoline.

To a solution of 3 g of 5β(10→9)abeo-9,10-didehydro-6-methyl-8β-methyl-12-bromoo-ergoline in 70 ml of dimethyl-formamide were added under nitrogen 3 g of cuprous iodide and 2 g of dried freshly prepared sodium methoxide.

The resulting mixture was stirred at 120° C. for 4 hours, then diluted with concentrated ammonium hydroxide solution and extracted with ethylacetate. The organic phase was washed with brine dried and evaporated. The residue was chromatographed on silica gel eluting with cyclohexane/ethyl acetate 5/2 providing 1.2 g of the title compound, m.p. 115–116° C.

EXAMPLE 25

5β(10→9)abeo-9,10-Didehydro-6-methyl-8β-methyl-12-cyano-ergoline.

Operating as in Example 24, but employing potassium cyanide instead of sodium methoxide and cuprous cyanide instead of cuprous iodide, the title compound was obtained in 30% yield, m.p. 102–105° C.

EXAMPLE 26

5β(10→9)abeo-9,10-Didehydro-2-thiomethyl-6-methyl-8β-methyl-13-methoxy-ergoline.

Operating as in Example 24, but employing 5β(10→9)abeo- 9,10-didehydro-2-thiomethyl-6-methyl-8β-methyl-13-bromo-ergoline instead of 5β(10→9)abeo-9,10-didehydro-6-methyl-8β-methyl-12-bromo-ergoline, the title compound was obtained in 35% yield, m.p. 124–127° C.

EXAMPLE 27

5β(10→9)abeo-9,10-Didehydro-2-thiomethyl-6-methyl-8β-methyl-13-cyano-ergoline.

Operating as in Example 24, but employing 5β(10→9)abeo-9,10-didehydro-2-thiomethyl-6-methyl-8β-methyl-13-bromo-ergoline instead of 5β(10→9)abeo-9,10-didehydro-6-methyl-8β-methyl-12-bromo-ergoline and potassium cyanide instead of sodium methoxyde and cuprous cyanide instead of sodium methoxide and cuprous cyanide instead of cuprous iodide, the title compound was obtained in 45% yield, m.p. 141–143° C.

EXAMPLE 28

5β(10→9)abeo-9,10-Didehydro-6-methyl-8β-methyl-12-aminocarbonyl-ergoline.

Operating as in Example 15, but employing 5β(10→9)abeo-9,10-didehydro-6-methyl-8β-methyl-12-cyano-ergoline instead of 5β(10→9)abeo-9,10-didehydro-2-cyano-6-methyl-8β-methyl-ergoline, the title compound was obtained in 65% yield, m.p. 151–155° C.

EXAMPLE 29

5β(10→9)abeo-9,10-Didehydro-2-thiomethyl-6-methyl-88-methyl-13-aminocarbonyl-ergoline.

A solution of 1.5 g of 5β(10→9)abeo-9,10-didehydro-2-thiomethyl-6-methyl-8β-methyl-13-cyano-ergoline and 1.5 g of ground potassium hydroxyde in 30 ml of tert-butanol was refluxed for 2 hours.

The precipitate was filtered off, washed with water and recrystallized from acetone furnishing 0.7 g of the title compound, m.p. 155–158° C.

EXAMPLE 30

5β(10→9)abeo-9,10-Didehydro-6-methyl-8β-methyl-13-aminocarbonyl-ergoline.

Operating as in Example 23, but employing 5β(10→9)abeo-9,10-didehydro-2-thiomethyl-6-methyl-8β-methyl-13-aminocarbonyl-ergoline, instead of 5β(10→9)abeo-9,10-didehydro-2-methylthio-6-methyl-8β-methyl-12-bromo-ergoline, the title compound was obtained in 30% yield, m.p. 138–141° C.

EXAMPLE 31

5β(10→9)abeo-9,10-Didehydro-6-methyl-8α-methyl-ergoline.

Operating as in Example 3, but employing 5β(10→9) abeo-9,10-didehydro-6-methyl-8α-(phenylsulphonyl) methyl-ergoline, instead of 5β(10–09)abeo-9,10-didehydro-6-methyl- 8β-(phenylsulphonyl)methyl-ergoline, the title compound was obtained in 40% yield, m.p. 185–190° C.

EXAMPLE 32
5β(10→9)abeo-9,10-Didehydro-1,6-dimethyl-8β-methyl-ergoline.

To a solution of 3 g of 5β(10→9)abeo-9,10-didehydro-6-methyl-8β-methyl-ergoline, in 30 ml of dimethyl sulphoxide was added to 0.6 g of freshly ground potassium hydroxide.

After stirring for 15', 1.2 g of methyliodide was added and the stirring was continued for 20'.

The green solution was diluted with water and partitioned with ethyl acetate. After washing with brine and dried, the solvent was removed and the residue filtered on a small pad of silica gel eluting with ethyl acetate. After crystallization from diethyl ether, 1.9 of the title compound was obtained, m.p. 126–128° C.

EXAMPLE 33
5β(10→9)abeo-2,3β-Dihydro-9,10-didehydro-6-methyl-8β-methyl-ergoline and 5β(10→9)abeo-2,3-Dihydro-9,10-didehydro-6-methyl-8β-methyl-ergoline.

To a stirred solution of 5 g of 5β(10→9)abeo-9,10-didehydro-6-methyl-8β-methyl-ergoline in 50 ml of trifluoroacetic acid, 1.7 g of sodium borohydride was added portionwise under nitrogen.

After 10' of stirring, the resulting reaction mixture was diluted with water, basified with ammonium hydroxide and extracted with ethyl acetate. After drying, the solvent was removed and the residue carefully chromatographed on silica gel eluting with ethyl acetate.

The fractions containing the less polar compound were pooled and the solvent removed.

Crystallization from diethylether afforded 3.1 g of 5β(10 9)abeo-2,3β-dihydro-9,10-didehydro-6-methyl-8β-methyl-ergoline, m.p. 179–182° C.

Continuing the elution with the eluent ethyl acetate/acetone g5/5, the more polar compound was collected, after crystallization from diisopropilether 0.35 g of 5β(10 9)abeo-2,3α-dihydro-9,10-didehydro-6-methyl-8β-methyl-ergoline was provided, m.p.143–148° C.

EXAMPLE 34
5β(10→9)abeo-2,3β-Dihydro-9,10-didehydro-1-acetyl-6-methyl-8β-methyl-ergoline.

To a solution of 2 g of 5β(10→9)abeo-2,3-dihydro-9,10-didehydro-6-methyl-8β-methyl-ergoline in 50 ml of ethyl acetate and 5 ml of triethylamine was added 1 g of acetic anhydride. After keeping for 2 h, the solution was washed with ammonium hydroxide, dried and evaporated. The residue was crystallized from isopropyl alcohol affording 1.8 of the title compound, m.p. 142–144° C.

EXAMPLE 35
5β(10→9)abeo-2,3α-Dihydro-9,10-didehydro-1-acetyl-6-methyl-8β-methyl-ergoline.

Operating as in Example 34, but employing 5β(10→9) abeo-2,3α-dihydro-9,10-didehydro-6-methyl-8β-methyl-ergoline, instead of 5β(10→9)abeo-2,3β-dihydro-9,10-didehydro-6-methyl-6β-methyl-ergoline, the title compound was obtained in 70% yield, m.p. 174–176° C.

EXAMPLE 36
5β(10→9)abeo-2,3β-Dihydro-9,10-didehydro-1-aminocarbonyl-6-methyl-8β-methyl-ergoline.

To a solution of 2 g of 5β(10→9)abeo-2,3β-dihydro-9,10-didehydro-6-methyl-8β-methyl-ergoline in 20 ml of hydrochloric acid 0.1 N was added portionwise 0.4 g of potassium cyanate at 0° C.

After stirring for 1 h, the solution was basified with ammonium hydroxide and extracted with methylene chloride.

After drying, the solvent was removed and the residue crystallized from acetone providing 1.3 g of the title compound, m.p. 220–222° C.

EXAMPLE 37
5α(10→9)abeo-9,10-Didehydro-6-methyl-8β-methyl-ergoline.

Operating as in Example 3, but employing 5α(10→9) abeo-9,10-didehydro-6-methyl-8β-(phenylsulphonyl) methyl-ergoline instead of 5β(10→9)abeo-9,10-didehydro-6-methyl-8β-(phenylsulphonyl)methyl-ergoline, the title compound was obtained in 20% yield, m.p. 146–148.

EXAMPLE 38
5β(10→9)abeo-6-Methyl-8β-methyl-10α-ergoline and 5β(10→9)-6-Methyl-8β-methyl-10β-ergoline.

A solution of 5 g of 5β(10→9)abeo-9,10-didehydro-6-methyl-8β-methyl-ergoline in 70 ml of ethanol and 2 g of Pd/C$_{10}$% was hydrogenated at 20 psi of hydrogen at room temperature. The catalyst was filtered off and the solvent was removed. The residue was carefully cromatographed on silica gel eluting with cyclohexane/acetone 1/1 providing 0.6 g of 5β(10→9)abeo-6-methyl-8β-methyl-10α-ergoline, m.p. 265–268.

Continuing the elution with cyclohexane/acetone 2/3, 1.2 g of 5β(10→9)abeo-6-methyl-8β-methyl-10-ergoline, m.p. 208–212° C. were further obtained.

EXAMPLE 39
5β(10→9)abeo-2,3β-Dihydro-9,10-didehydro-6-methyl-8β-methyl-12-bromo-ergoline To a stirred solution of 2 g of 5β(10→9)abeo-1-acetyl-2, 3β-dihydro-9,10-didehydro-6-methyl-8β-methyl-ergoline in 30 ml of acetic acid was added dropwise 1,2 g of bromine. After stirring for 1 hour, the resulting solution was diluted with ethyl acetate and partitioned with a 0.1 M solution of sodium hydroxide.

After drying the solvent was removed in vacuo and the resulting reaction product was dissolved in 100 ml of 0.1 M of hydrochloric acid and refluxed for 2 hours. The resulting solution was basified with a concentrate solution of ammonium hydroxide and further extracted with ethyl acetate.

After drying amd removal of the solvent, the crude product was crystallized from acetone affording 1.3 g of the title compound, m.p. 175–178° C.

EXAMPLE 40
5β(10→9)abeo-2,3β-Dihydro-9,10-didehydro-6-methyl-8β-methyl-12 nitro-ergoline.

To a stirred solution of 5 g of 5β(10→9)abeo-2,3β-dihydro-9,10-didehydro-1-acetyl-6-methyl-8β-methyl-ergoline in 50 ml of concentrate sulphuric acid was added dropwise 3 ml of concentrate nitric acid at room temperature.

After stirring for ½ hours, the yellow reaction mixture was poured into crushed ice and basified with concentrate solution of ammonium hydroxide.

Extraction with ethyl acetate, drying and removal of the solvent afforded a crude reaction mixture that was carefully chromographed on silica gel eluting with ethyl acetatatecyclohexane 5/3.

The fractions were pooled affording 3.8 g of a mixture of 5β(10→9)abeo-2,3β-9,10-didehydro-1 acetyl-6-methyl-8β-methyl-12 nitro-ergoline accompanied by the isomer 5β(10→9)abeo-2,3β-9,10-didehydro-1-acetyl-6-methyl-8β-methyl 14 nitro-ergoline.

The mixture was dissolved in 100 ml of 0.1 M solution of hydrochloric acid and refluxed for ½ hours.

After basification and extraction with ethyl acetate, the reaction mixture was crystallised from boiling ethanol affording 1.7 g of the title compound, m.p. 189–193° C.

EXAMPLE 41

5β(10→9)abeo-2,3β-Dyhydro-9,10-didehydro-6-methyl-8β-methyl-14-nitro ergoline.

The mother liquor of crystallization of 5β(10→9)abeo-2,3β-dihydro-9,10-didehydro-6-methyl-8β-methyl-12-nitro-ergoline was carefully columned on silica gel eluting with acetate/ciclohexane 2/1.

After evaporation of the solvent, the residue was crystallized twice from acetone, leading to 0.6 g of the title compound, m.p. 156–159° C.

EXAMPLE 42

5β(10→9)abeo-9,10-Didehydro-6-methyl-8β-methyl-14-nitro ergolina.

To a solution of 1.5 g of 5β(10→9)-2,3β-dihydro-9,10-didehydro-6-methyl-8β-methyl-12-nitro-ergolina in 75 ml of dichloromethane was added 5 g of freshly prepared manganese dioxide.

After stirring for 8 hours the suspension was filtered over celite.

The solvent was removed and the residue dissolved in acetone and charcoalized.

By concentration, 0.84 g of the titled compound were obtained, m.p. 197–203° C.

What is claimed is:

1. A compound represented by formula I":

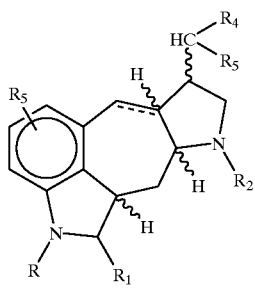

I"

wherein $R_1$ is a hydrogen, chlorine or bromine atom or a methyl, methylthio, hydroxy, cyano, nitro or carboxamido group;

$R_2$ is $C_1$–$C_3$ alkyl or an allyl group;

$R_3$ and $R_4$ are independently a hydrogen atom, a linear or branched $C_1$–$C_5$ alkyl group, a linear or branched $C_3$–$C_5$ alkenyl group, a $C_5$–$C_6$ cycloalkyl $C_1$–$C_3$ alkyl group, a phenyl-$C_1$–$C_3$ alkyl, a phenyl-$C_3$–$C_5$ alkenyl or phenyl group:

which groups are optionally substituted by $C_1$–$C_3$ alkyl, $C_1$–$C_3$ alkoxy, trifluoromethyl, hydroxy or amino group; or a group of the formula

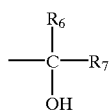

wherein $R_6$ is a hydrogen atom or a $C_1$–$C_3$ alkyl group and $R_7$ is a phenyl group or a substituted phenyl group as described above;

between positions 9–10 represents a single or a double bond;

$R_5$ is a hydrogen, bromine, fluorine or iodine atom or a methoxy, cyano, carboxamido, nitro, methylthio or trifluoromethyl or a group of the formula $NR_8R_9$ wherein $R_8$ and $R_9$ are independently a hydrogen atom, or a $C_{1-3}$ alkyl, acetyl, methanesulphonyl or trifluoroacetyl group; and R represents a hydrogen atom or a $C_{1-5}$ linear or branched alkyl, methanesulphonyl or acetyl group or a group of the formula $CONR_8R_9$ wherein $R_8$ and $R_9$ are as defined above;

or a pharmaceutically acceptable salt thereof.

2. The compound of claim 1, or a pharmaceutically acceptable salt thereof, wherein $R_1$ represents a hydrogen atom, a cyano group, or a carboxamido group, $R_2$ represents a methyl group, $R_3$ represents a hydrogen atom, $R_4$ represents a group of the formula —CH(OH)Ph, $R_5$ represents hydrogen, fluorine, iodo, methoxy, methylthio, trifluoromethyl, nitro, a carboxamido group, or a group of the formula $NR_8R_9$, wherein $R_8$ and $R_9$ are, independently, a hydrogen atom or a $C_{1-3}$ alkyl, acetyl, methanesulphonyl or trifluoroacetyl group, and the hydrogen atom at position 5 and the residue at position 8 are both β.

3. The compound of claim 1, or a pharmaceutically acceptable salt thereof, wherein the 9–10 positions are bonded by a double bond.

4. The compound of claim 1, or a pharmaceutically acceptable salt thereof, wherein the 9–10 positions are bonded by a single bond.

5. The compound of claim 1, or a pharmaceutically acceptable salt thereof, which is 5β-(10→9)abeo-2,3β-dihydro-9,10-didehydro-6-methyl-8β-methyl-ergoline.

6. The compound of claim 1, or a pharmaceutically acceptable salt thereof, wherein $R_5$ is a bromine, fluorine or iodine atom or a methoxy, cyano, carboxamido, nitro, methylthio, trifluoromethyl or a group of the formula $NR_8R_9$, wherein $R_8$ and $R_9$ are as defined above.

7. The compound of claim 1, or a pharmaceutically acceptable salt thereof, wherein $R_3$ is a phenyl-$C_1$–$C_3$ alkyl, a phenyl-$C_3$–$C_5$ alkenyl or a phenyl group, wherein these groups are optionally substituted by a $C_1$–$C_3$ alkyl, $C_1$–$C_3$ alkoxy, trifluoromethyl, hydroxy or an amino group, or $R_3$ is a group of the formula -C(OH)$R_6R_7$, wherein $R_6$ is a hydrogen atom or a $C_1$–$C_3$ alkyl group and $R_7$ is a phenyl group, or a phenyl group substituted with a $C_1$–$C_3$ alkyl, $C_1$–$C_3$ alkoxy, trifluoromethyl, hydroxy or an amino group.

8. The compound of claim 1, or a pharmaceutically acceptable salt thereof, wherein $R_1$ is a chlorine or bromine atom or a methyl, methylthio, hydroxy, cyano, nitro or carboxamido group.

9. The compound of claim 1, or a pharmaceutically acceptable salt thereof, wherein R is a $C_{1-5}$ linear or branched alkyl, methanesulphonyl, acetyl or a group of the formula $CONR_8R_9$, wherein $R_8$ and $R_9$ are as defined above.

* * * * *